United States Patent [19]

Beers et al.

[11] Patent Number: 5,783,597

[45] Date of Patent: Jul. 21, 1998

[54] 2,5-DISUBSTITUTED THIOPHENES: INHIBITORS OF 5-LIPOXYGENASE AND INDUCIBLE CYCLOOXYGENASE (COX-2) ENZYMES, COMPOSITION AND USE

[75] Inventors: Scott Alan Beers, Flemington; Michael Paul Wachter, Bloomsbury, both of N.J.

[73] Assignee: Ortho Pharmaceutical Corporation, Raritan, N.J.

[21] Appl. No.: 810,848

[22] Filed: Mar. 4, 1997

[51] Int. Cl.$^6$ .................. A61K 31/38; C07D 333/36; C07D 333/42

[52] U.S. Cl. ............... 514/447; 514/445; 549/63; 549/68

[58] Field of Search .................. 514/445, 447; 549/63, 68

[56] References Cited

U.S. PATENT DOCUMENTS

| | | | |
|---|---|---|---|
| 3,657,432 | 4/1972 | Shen et al. | 549/63 |
| 3,963,750 | 6/1976 | Goudie | 549/68 |
| 4,826,868 | 5/1989 | Wachter et al. | 514/407 |
| 4,877,809 | 10/1989 | Binder et al. | 549/63 |
| 5,164,381 | 11/1992 | Wachter et al. | 514/85 |
| 5,242,940 | 9/1993 | Wachter et al. | 514/406 |
| 5,298,521 | 3/1994 | Ferro | 514/406 |
| 5,387,602 | 2/1995 | Ferro | 514/406 |
| 5,403,857 | 4/1995 | Edwards et al. | 514/432 |
| 5,501,018 | 3/1996 | Appell et al. | 403/5 |
| 5,571,821 | 11/1996 | Chan et al. | 514/312 |

OTHER PUBLICATIONS

S. A. Beers et al., In Vitro and Invivo Pharmacology of RWJ 63556, a Potent, Orally Active 5-Lo Inhibitor with Specific COX-2 Ihnibitory Activity, Abstract #P49, Eight International Congress of the Inflammation Research Association, Oct. 28, 1996, Hersey PA.

Saida et al, "Preparation of Phenoxythiophene Derivatives", CA115:255987, 1991.

Primary Examiner—Deborah C. Lambkin
Attorney, Agent, or Firm—Kenneth J. Dow

[57] ABSTRACT

2,5-Disubstituted thiophene derivatives, and more particularly, to 2-aryloxy-5-alkansulfonamido-thiophenes of the general formula:

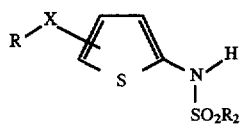

Wherein, $R_2$ is $CF_3$, $C_1$–$C_{10}$ alkyl, or phenyl;

X is O, S, or $CH_2$; and

R is aryl, $C_1$–$C_{10}$ alkyl, or $C_3$–$C_8$ cycloalkyl; which compounds are pharmacologically active in alleviating inflammation, asthma, arthritis, hypersensitivity, myocardial ischemia and dermatological conditions, such as, psoriasis and dermatitis, and gastrointestinal inflammatory conditions, such as, inflammatory bowel syndrome.

16 Claims, 1 Drawing Sheet

FIG. 1 EFFECT OF THE COMPOUND OF EXAMPLE 1 ON EX VIVO $LTB_4$ PRODUCTION IN DOG WHOLE BLOOD (5 HR POST DOSING)

2,5-DISUBSTITUTED THIOPHENES: INHIBITORS OF 5-LIPOXYGENASE AND INDUCIBLE CYCLOOXYGENASE (COX-2) ENZYMES, COMPOSITION AND USE

The present invention relates to 2,5-disubstituted thiophene derivatives, and more particularly, to 2-aryloxy-5-alkansulfonamido-thiophenes which are pharmacologically active in alleviating inflammation, asthma, arthritis, hypersensitivity, myocardial ischemia and dermatological conditions, such as, psoriasis and dermatitis, and gastrointestinal inflammatory conditions, such as, inflammatory bowel syndrome.

BACKGROUND OF THE INVENTION

Non-steroidal Antiinflammatory drugs (NSAIDs) such as indomethacin, naproxen, piroxicam, diclofenac and the like have been shown to alleviate inflammation. Their mode of action has been generally attributed to their ability to inhibit the enzyme cyclooxygenase (CO), a key enzyme in the arachidonic cascade, which attenuates the biosynthesis of various prostaglandins. The prostaglandin end-products of the cyclooxygenase pathway are responsible for many of the early signs of inflammation including increases in vascular permeability leading to edema, hyperalgesia and pyrexia.

The other major pathway of arachidonic acid (AA) metabolism is the lipoxygenase pathway. Lipoxygenase products of arachidonate metabolism such as the leukotrienes (LTs), hydroxyeicosatetraenoic acids (HETEs) and hydroperoxyeicosatetraenoic acids (HPETEs) have been implicated in disease states including acute and chronic inflammation, arthritis, allergic and other hypersensitivity disorders, and various dermatological, cardiovascular, hyperalgesic and gynecological disorders. In particular, the LTs which are the products of 5-lipoxygenase (5-LO) catalyzed oxygenation of AA participate in a variety of chronic and acute inflammatory diseases. Leukotriene $B_4$ ($LTB_4$), a key LT product, is believed to play a role in chronic inflammatory conditions such as rheumatoid arthritis. $LTB_4$ is chemotactic to inflammatory cells and helps to contribute to the chronic influx of leukocytes into the synovial fluid which eventually results in joint erosion.

Pharmacologically active compounds that can inhibit both enzyme pathways at similar concentrations have the potential to provide more complete relief for patients suffering from arthritis and inflammatory, hypersensitivity, dermatological, cardiovascular, gastrointestinal, ocular and gynecological disorders. An example of such a compound is the antiinflammatory agent 3-[5-(4-chlorophenyl)- 1-(4-methoxyphenyl)-3-pyrazolyl]-N-hydroxy-N-methyl propanamide, tepoxalin, which is one of a series of 1,5-diaryl-3-substituted pyrazoles disclosed in U.S. Pat. Nos. 5,164,381 and 4,826,868 (Wachter & Ferro). Other 1,5-diaryl-pyrazoles which act as dual 5-LO and CO inhibitors and possess antiinflammatory activity are described in U.S. Pat. Nos. 5,051,018; 5,242,940; 5,298,521 and 5,387,602.

Recently, the cyclooxygenase enzyme was shown to exist as two isoforms: COX-1 and COX-2 [(Medicinal Chemistry Research, Vol. 5, No. 5, pp 319–408 (1995)]. COX-1, which is constituitively expressed, is present in tissues such as stomach, gut or kidney where prostaglandins have a cytoprotective effect in maintaining normal physiological processes. COX-2, which is induced or stimulated by inflammatory or mitogenic stimuli, is the probable primary target in inflammatory disease states and its selective inhibition vs COX-1 provides an opportunity to inhibit the inflammatory, pyretic and thrombogenic effects of prostaglandins while avoiding the ulcerogenic and nephrotoxic side effects that result from non-selective inhibition.

The present invention describes compounds that are dual inhibitors of both the 5-LO and COX-2 enzymes. In addition, these compounds selectively inhibit COX-2 as opposed to COX-1, and possess the ability to reduce inflammation without the side effects on the gastric mucosa and kidney which are associated with previous NSAID therapy.

SUMMARY OF THE INVENTION

The present invention provides 2,3 and 2,5-disubstituted thiophenes, their use and a method of their synthesis. The compounds of this invention are pharmacologically active in alleviating inflammation and inhibit the cyclooxygenase pathway primarily via COX-2, the lipoxygenase pathway, or preferably both pathways.

In particular, the invention provides a thiophene derivative of general formula I

Wherein, $R_2$ is $CF_3$, $C_1$–$C_{10}$ alkyl, or phenyl;

X is O, S, or $CH_2$; and

R is aryl, $C_1$–$C_{10}$ alkyl, or $C_3$–$C_8$ cycloalkyl wherein aryl refers to a phenyl or naphthyl moiety which may be substituted by one or more of the following: halogen, $CF_3$, $C_1$ –$C_4$ alkyl, alkoxy, alkylthio, or alkylsulfonyl; and the pharmaceutically acceptable salts, esters and pro-rug forms thereof.

Preferred compounds of the invention are encompassed by the following general formula II.

Wherein, $R_1$ is halogen, $CF_3$, $C_1$ –$C_4$ alkyl, alkoxy, alkylthio, or alkylsulfonyl.

The present invention also contemplates a pharmaceutical composition that comprises an antiinflammatory amount of an above-described substituted thiophene compound dispersed in a pharmaceutically acceptable carrier. The dose may be administered by topical, oral parenteral or aerosol routes. In preferred practice, an amount of those compounds of the invention capable of inhibiting both the cyclooxygenase and the lipoxygenase pathways are utilized in the composition when the composition is administered to a mammal.

Further contemplated is a method for alleviating inflammation in a mammal exhibiting an inflammatory condition. The method comprises administering to such mammal a pharmaceutical composition that includes as active ingredient an effective amount of a compound of the present invention in association with a pharmaceutically acceptable carrier for topical, oral, parenteral or aerosol administration.

DETAILED DESCRIPTION OF THE INVENTION

The preferred 2,5-disubstituted thiophene compounds of the invention in which X=O can be prepared according to Scheme 1.

Treatment of 2-Nitro-5-bromothiophene A with the appropriately substituted phenol B in DMF with a base such as potassium carbonate gives the corresponding 2-nitrothiophene ether C. The ether C is dissolved in acetic acid and treated with acetic anhydride and Fe powder to yield the corresponding acetamide D. The acetamide is dissolved in an inert solvent such as tetrahydrofuran, cooled to −78° and treated with a base such as lithium diisopropylamide followed by treatment with methanesulfonyl chloride. The intermediate disubstituted amino derivative is evaporated to dryness and redissolved in ethanol and then treated with ammonium hydroxide to give the desired methansulfonamide E.

To prepare the 2,5-disubstituted thipohene compounds of the invention where R is alkyl or cycloalkyl, the appropriately alkanol or cycloalkanol compound can be substituted for the phenol B in the foregoing reaction scheme.

The 2,5-disubstituted thiophene compounds of the invention in which X=S can be prepared according to Scheme 2.

R = aryl, cycloalkyl, n-alkyl

The compounds of general structure F were synthesized from compound A according to the method described above utilizing the appropriate thiol in place of a phenol. Conversion of compounds F to compounds H is accomplished following a similar procedure as that outlined in Scheme 1.

The 2,5-disubstituted thiophene compounds of the invention in which X=CH$_2$ can be prepared according to Scheme 3.

Scheme 3

Treatment of 5-Nitrothiophene-2-carboxaldehyde I with an appropriately substituted arylmagnesium bromide in an inert solvent such as THF yields the alcohol J. Deoxygenation of the alcohol is carried out with triethylsilane and BF$_3$ etherate to give compound K. Conversion of the nitro functionality in K to the methanesulfonamido group in M is carried out as described for for the corresponding analogs in Scheme 1.

The 2,5disubstituted thiophene compounds of the invention in which X=a single bond can be prepared according to Scheme 4.

Treatment of compound A with a Pd(0) catalyst such as tetrakis(triphenylphos- phine)palladium(0) in a solvent such as toluene in the presence of an arytboric acid represented by N yields the biaryl coupling product O. Conversion of the nitro group of O to methansulfonamide Q is carried out as described for Scheme 1.

The 2,5disubstituted thiophene compounds of the invention in which $R_2=C_2-C_{10}$ alkyl and phenyl can be prepared according to Scheme 5.

Acetamide D, the synthesis of which was described in Scheme 1, is dissolved in an inert solvent such as tetrahydrofuran, cooled to −78° and treated with a base such as lithium diisopropylamide followed by treatment with the appropriate alkyl or arylsulfonyl chloride. The intermediate disubstituted amino derivative is evaporated to dryness and redissolved in ethanol and then treated with ammonium hydroxide to give the desired sulfonamide R.

2,3-disubstituted thiophene compounds of the invention in which X=O can be prepared according to Scheme 6.

2-Nitro-3-bromothiophene is dissolved in a solvent such as DMF and treated with a base such as potassium carbonate and an appropriately substituted phenol at a temperature of 80° C. to give the aryl ether T. The nitro ether is reduced with tin powder in concentrated HCl at 60° C. to yield the tin double salt U. The salt is dissolved in pyridine, cooled to 0° C. and treated with methanesulfonyl chloride to give the 2,3-disubstituted thiophene methanesulfonamide V.

The foregoing reactions are performed in a solvent appropriate to the reagents and materials employed and suitable for the transformation being effected. It is understood by those skilled in the art of organic synthesis that the various functionalites present on the molecule must be consistent with the chemical transformations proposed. This will frequently necessitate judgment as to the order of synthetic steps, protection of reactive groups, and selection of reaction conditions. Reaction conditions compatible with the substituents employed will be apparent to one skilled in the art, as will be the selection of protecting groups where needed.

From formula 1 it is evident that some of the compounds of the invention may have one or more asymmetrical carbon atoms in their structure. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereospecific reactions.

Suitable pharmaceutical salts are those of inorganic or organic acids, such as hydrochloric acid, hydrobromic acid, hydroiodic acid, sulfuric acid, nitric acid, phosphoric acid, acetic acid, succinic acid, oxalic acid, malic acid and the like. Suitable salts are also those of inorganic or organic bases, such as KOH, NaOH, Ca(OH)$_2$, Al(OH)$_3$, piperidine, morpholine, ethylamine, triethylamine and the like.

Also induced within the scope of the invention are the hydrated forms of the compounds which contain various amounts of water, for instance, the hydrate, hemihydrate and sesquihydrate forms.

The substituted thiophene compounds of the invention are capable of inhibiting the lipoxygenase enzyme pathway and/or the cycolooxygenase 2 (COX-2) enzyme pathway to achieve the desired pharmacological result. In preferred practice, the 1,5 -disubstituted thiophene compound of the pharmaceutical composition is capable of inhibiting both the cyclooxygenase and the lipoxygenase enzyme pathways in the amount in which the compound is present in the composition, when the composition is administered as a unit dose in the appropriate mammal to be treated.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacological acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.01 mg/kg to about 500 mg/kg of animal body weight, preferably given in divided doses two to four times a day, or in sustained release form. For most large mammals the total daily dosage is from about 10 to about 2000 milligrams, preferably from about 100 mg to 1000 mg. Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. Veterinary dosages correspond to human dosages with the amounts administered being in proportion to the weight of the animal as compared to adult humans.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

EXAMPLES

Method 1: General Procedure for the Synthesis of Compounds E

2-Nitro-5bromothiophene (1 equivalent) is dissolved in dimethylformamide (3 mL per mmol) and to the resulting solution is added the appropriately substituted phenol (1 equivalent) and potassium carbonate (2 equivalents). This mixture is stirred at 70° C. for 4–8 hours and then poured into water and the crude solid filtered and washed with water to give the intermediate 2-Nitro-5-phenoxy-thiophene.

The above substituted 2-nitro-5-phenoxythiophene (1 equivalent) is dissolved in acetic acid (3 mL per mmol) and treated with acetic anhydride (1 equivalent) and iron powder (4 equivalents). The resulting mixture is heated at 80° C. for 4–8 hours and then poured into water and the crude solid filtered and purified via chromatography on silica gel to yield the desired 2-acetamido-5-phenoxy thiophenes.

The 2-acetamido-5-phenoxy thiophene (1 equivalent) is dissolved in THF (7.5 mL per mmol) and cooled to −78° C. Lithium diisopropylamide (1.1 equivalents) is added and the solution stirred for an additional ten minutes before methanesulfonyl chloride (1.1 equivalents) is added. After 1–2 hours the mix is evaporated in vacuo and redissolved in ethanol. Concentrated ammonium hydroxide (0.5 mL per mmol) is added and after 30–60 minutes the mixture is again evaporated in vacuo. The residue is partitioned between methylene chloride and 1N HCl. The organic layer is washed with water, dried over magnesium sulfate and concentrated in vacuo. The resulting 2-methane-sulfonamido-5-phenoxy thiophene is purified via silica gel column chrom-atography eluted with hexane-ethyl acetate 1:1.

Example 1

A specific procedure for the synthesis of:

N-[(4-fluoro)-5-phenoxythien-2-yl]methanesulfonamide (1)

2-Nitro-5-bromothiophene (2.97 g, 14.2 mmol) was dissolved in dimethyl-formamide (40 mL). To this was added 4-fluorophenol (1.59 g, 14.2 mmol) and potassium carbonate (3.92 g, 28.4 mmol). This was stirred at 70° C. for 5 hours after which time the mix was poured into water and the crude solid was filtered and washed with water to give 2-Nitro-5(4-fluoro)phenoxythiophene 2.67 g (78%), mp=69°–70° C.

2-Nitro-5-(4-fluoro)phenoxythiophene (2.44 g, 10.2 mmol) was dissolved in acetic acid (20 mL). To this was added acetic anhydride (20 mL) and iron powder (2.28 g, 40.8 mmol). This was stirred at 80° C. for 5 hours. The mix was then poured into water and the crude solid was filtered and purified on a silica gel column eluted with ethyl acetate-hexane 1:1 giving 1.10 g (43%) of N-[(4-fluoro)-5-phenoxythien-2-yl]acetamide, mp=116.8–117.5° C.

N-[(4-fluoro)-5-phenoxythien-2-yl]acetamide (1.0 g, 3.98 mmol) was dissolved in tetrahydrofuran (30 mL) and cooled to −78° C. Lithium diisopropylamide (3.0 mL of a 1.5M sol'n) was added and this was stirred for an additional ten minutes before methanesulfonyl chloride (0.35 mL, 4.5 mmol) was added. After one hour the mix was evaporated in vacuo and redissolved in ethanol. Concentrated ammonium hydroxide (2 mL) was added and after 30 minutes the mixture was again evaporated in vacuo. The residue was partitioned between methylene chloride and 1N HCl. The organic layer was washed with water, dred over magnesium sulfate and concentrated in vacua. The product was purified using silica gel column chromatography eluted with hexane-ethyl acetate 1:1 giving N-[(4-fluoro)-5-phenoxythien-2-yl] methanesulfon-amide, 0.79 g (69%), Mp 94°–95° C. $^1$HNMR (CDCl$_3$) $\partial$3.08 (s, 3H, CH$_3$), 6.27 (d,1H, Th H), 6.72 (d,1H, Th H), 7.07 (m, 4H, Ar). CIMS (m/e) 288 (MH$^+$). Anal Calcd for C$_{11}$H$_{10}$FNO$_3$S$_2$: C 45.98; H 3.51; N 4.87.

Found: C 45.78; H 3.62; N 4.67.

The compounds of Table 1 were prepared according to the general procedure described above in method 1 and Example 1.

TABLE 1

| Example Number | R$_1$ | Melting Point °C. | Analysis$^+$ C,H,N | % yield | Mass Spectrum m/e (M$^+$) |
|---|---|---|---|---|---|
| 2 | H | 78–79 | x,x,x | 49 | 270 |
| 3 | 3-F | 75.5–77 | x,x,x | 49 | 288 |
| 4 | 4-SCH$_3$ | 141–141.5 | x,x,x | 67 | 316 |
| 5 | 4-SO$_2$CH$_3$ | 140–141 | x,x,x | 34 | 348 |
| 6 | 3-Cl,4-F | gum | x,x,x* | 52 | 339@ |
| 7 | 4-OCH$_3$ | 75.4–75.7 | x,x,x | 41 | 300 |
| 8 | 3-Cl | 84–86.5 | x,x,x | 66 | 304 |
| 9 | 2,3-diCH$_3$ | 140–141.4 | x,x,x | 47 | 298 |
| 10 | 3-CF$_3$ | 59–60 | x,x,x | 60 | 338 |
| 11 | 3-CH$_3$,4-F | 100–101 | x,x,x | 42 | 302 |
| 12 | 4-Cl | 98–99.5 | x,x,x | 32 | 304 |
| 13 | 2,4-diCl | 83.5–84.5 | x,x,x | 12 | 338 |
| 14 | 2,4-diF | 75 | x,x,x | 71 | 306 |
| 15 | 3-CH$_3$ | 88–90 | x,x,x | 55 | 284 |
| 16 | 2-CH$_3$,4-F | 86–86.5 | x,x,x | 64 | 302 |
| 17 | 2-Br,4-F | 99.6–101.9 | x,x,x | 62 | 367 |
| 18 | 3,5-diCF$_3$ | 114–116 | x,x,x | 71 | 406 |
| 19 | 2-Cl,5-CF$_3$ | gum | x,x,x | 52 | 372 |
| 20 | 3-i-Pr | gum | x,x,x |  | 312 |

Substitution of 1-naphthol, 2-naphthol or 5,6,7,8-tetrahydro-1-naphthol for the phenol in the general procedure described above gives the compounds of Table 1 B.

TABLE 1B

| Example Number | Aryl Ring | Melting Point °C. | Analysis$^+$ C,H,N | Mass Spectrum m/e (M$^+$) |
|---|---|---|---|---|
| 21 | 1-Naphthyl | 102–105.5 | x,x,x | 320 |
| 22 | 2-Naphthyl | 122–122.5 | x,x,x | 320 |
| 23 | 5,6,7,8-Tetrahydro-1-naphthyl | 112–116 | x,x,x | 324 |

Method 2: General Procedure for the Synthesis of Compounds R

The appropriate 2-acetamido-5-phenoxy thiophene (1 equivalent), synthesized as described above, is dissolved in THF (7.5 mL per mmol) and cooled to −78° C. Lithium diisopropylamide (1.1 equivalents) is added and the solution stirred for an additional ten minutes before the appropriate alkyl or aryl sulfonyl chloride (1.1 equivalents) is added.

After 1–2 hours the mix is evaporated in vacuo and redissolved in ethanol. Concentrated ammonium hydroxide (0.5 mL per mmol) is added and after 30–60 minutes the mixture is again evaporated in vacuo. The residue is partitioned between methylene chloride and 1N HCl. The organic layer is washed with water, dried over magnesium sulfate and concentrated in vacuo. The resulting 2-alkyl or arylsulfonamido-5-phenoxy thiophene is purified via silica gel column chromatography eluted with hexane-ethyl acetate.

The compounds of Table 2 were prepared according to the general procedure described above in Method 2.

TABLE 2

| Example Number | R₂ | Melting Point °C. | Analysis⁺ C,H,N | % yield | Mass Spectrum m/e (M⁺) |
|---|---|---|---|---|---|
| 24 | n-Butyl | gum | x,x,x | 64 | 312 |
| 25 | i-Propyl | 185–194 | x,x,x | 7 | 298 |
| 26 | n-Octyl | 35–40.5 | x,x,x | 64 | 368 |
| 27 | Phenyl | 96–110.5 | x,x,x | 9 | 332 |

Method 3: General Procedure for the Synthesis of Compounds H

2-Nitro-5-bromothiophene (1 equivalent) is dissolved in dimethylformamide (3 mL per mmol) and to the resulting solution is added the appropriately substituted aryl or alkyl thiol (1 equivalent) and potassium carbonate (2 equivalents). This mixture is stirred at 70° C. for 4–8 hours and then poured into water and the crude solid filtered and washed with water to give the intermediate 2-Nitro-5-arylthio- or 2-Nitro-5 -alkylthio-thiophene.

The above substituted thiophene is converted to the corresponding thiophenoxy and thioalkoxy derivatives as described above for the above 2-methane-suffonamido-5-phenoxy thiophenes.

The compounds of Table 3 were prepared according to the general procedure described above in Method 3.

TABLE 3

| Example Number | R | Melting Point °C. | Analysis⁺ C,H,N | Mass Spectrum m/e (M⁺) |
|---|---|---|---|---|
| 28 | Phenyl | 115–118 | x,x,x | 286 |
| 29 | cyclohexyl | 63–64 | x,x,x | 292 |
| 30 | n-Pentyl | oil | x,x,x | 280 |

Method 4: General Procedure for the Synthesis of Compounds M

5Nitrothiophene-2-carboxaldehyde (1 equivalent) is dissolved in anhydrous tetrahydrofuran (2.5 mL per mmol), after cooling to −78° C., the appropriate arylmagnesium bromide (1.1 equivalents) is added and the resulting mixture stirred for 30 minutes before quenching with aqueous ammonium chloride. The product is extracted with ethyl acetate and the organic layer washed with water, dried over magnesium sulfate and concentrated to give the 5-Nitrothiophene-2-phenylmethylcarbinol which is purified via silica gel chromatography.

To the above 5-Nitrothiophene-2-phenylmethylcarbinol (1 equivalent) in methylene chloride (2 mL per mmol) is added triethylsilane (3 equivalents). The reaction mix is cooled to 0° C. and borontrifluoride etherate (3 equivalents) is added and the reaction stirred for 16 hours, saturated aqueous sodium carbonate is added and the product extracted with ether. The organic layer is washed with water, dried over magnesium sulfate and evaporated in vacuo to give the 5-benzyl-2-nitro-thiophene derivative.

The above substituted 5-benzyl-2-nitro-thiophene (1 equivalent) is dissolved in acetic acid (3 mL per mmol) and treated with acetic anhydride (1 equivalent) and iron powder (4 equivalents). The resulting mixture is heated at 80° C. for 4–8 hours and then poured into water and the crude solid filtered and purified via chromatography on silica gel to yield the desired 2-acetamido-5-benzyl-thiophenes.

The 2-acetamido-5-benzyl thiophene (1 equivalent) is dissolved in THF (7.5 mL per mmol) and cooled to −78° C. Lithium diisopropylamide (1.1 equivalents) is added and the solution stirred for an additional ten minutes before methanesulfonyl chloride (1.1 equivalents) is added. After 1–2 hours the mix is evaporated in vacuo and redissolved in ethanol. Concentrated ammonium hydroxide (0.5 mL per mmol) is added and after 30–60 minutes the mixture is again evaporated in vacua. The residue is partitioned between methylene chloride and 1 N HCl. The organic layer is washed with water, dried over magnesium sulfate and concentrated in vacuo. The resulting 2-methane-sulfonamido-5-benzyl thiophene is purified via silica gel column chromatography eluted with hexane-ethyl acetate.

Example 31

A specific procedure for the synthesis of N-(5-Benzylthien-2-yl)methanesulfonamide (31)

5-Nitrothiophene-2-carboxaldehyde (3.11 g, 20.0 mmol) was dissolved in anhydrous tetrahydrofuran (50 mL). After cooling to −78° C. phenylmagnesium bromide (22 mls of 1N sol'n in THF) was added and stirred for 30 minutes before quenching with aqueous ammonium chloride. The product was extracted with ethyl acetate and the organic layer was washed with water, dried over magnesium sulfate and concentrated to an oil which was purified on a silica gel column eluted with hexane-ethyl acetate 4:1 yielding 3.72 grams of 5-Nitro-thiophene-2-phenylmethylcarbinol (79%) as a dark brown oil.

To the above alcohol (1.05 g, 4.46 mmol) in methylene chloride (10 mL) was added triethylsilane (2.20 mL, 13.5 mmol). The reaction mix was cooled to 0° C. and boron trifluoride etherate (1.66 mL, 13.5 mmol) was added and the reaction was stirred for 16 hours after which time 50 mL of saturated aqueous sodium carbonate was added. The product was extracted with ether, the ether layer was washed with water, dried over magnesium sulfate and evaporated in vacuo to give 2-benzyl-5-nitrothiophene as a brown oil (0.78 grams, 79%).

To 2-benzyl-5-nitrothiophene (1.88 g, 8.57 mmol) dissolved in 50 mL of a 1:1 mix of acetic acid-acetic anhydride was added iron powder (1.92 g, 34.4 mmol). The resulting mixture was vigorously stirred with a mechanical stirrer at 80° C. for 5 hours before being poured into ice water. The crude solid was filtered, washed with water and purified on a silica gel column eluted with hexane-ethyl acetate 5:2 giving N-(5-Benzylthien-2-yl)acetamide [0.930 g (47%)]. Mp 141–142° C.

The above acetamide (0.82 g, 3.5 mmol) was dissolved in anhydrous THF (25 mL). This solution was cooled to –78° C., lithium diisopropylamide (2.33 mL of 1.5N sol'n) added and after 10 minutes methanesulfonyl chloride (0.27 mL, 3.5 mmol) was added and the mix was stirred at room temperature for one hour before being evaporated in vacuo. The residue was resolved in 50 mL of methanol and 5 mL of concentrated ammonium hydroxide was added, stirred for one hour and evaporated in vacuo. The product was partitioned between methylene chloride and 1N HCl. The organic layer was washed with water, dried over sodium sulfate, concentrated in vacuo and purified on a silica gel column eluted with hexane-ethyl acetate 3:1 giving the title compound [0.51 g (55%)] as a yellow solid. Mp 91°–92° C., CIMS (m/e) 268 (MH⁺).

Method 5: General Procedure for the Synthesis of Compounds Q

2-Bromo-5-nitrothiophene (1 equivalent) is dissolved in toluene (3 mL per mmol) and to this solution is added the appropriate aryl boronic acid (1.08 equivalents), tetrakis (triphenylphosphine)palladium (0) (3 mole%), potassium carbonate (2 equivalents) and water (1.5 mL per mmol). The resulting mixture is refluxed for 18 hours after which time the layers are separated, the organic layer is evaporated to a crude solid which is recrystallized from ethanol-water to give the desired 2-nitro-5-aryl-thiophene.

The above 2-nitro-5-aryl-thiophenes are converted to the corresponding N-5-aryl-thien-2-yl]methanesulfonamides by the methods previously described above.

Example 32

A specific procedure for the synthesis of:

N-5-[(4-fluoro)phenyl-thien-2-yl]methanesulfonamide (32)

2-Bromo-5-nitrothiophene (3.50 g, 16.8 mmol) was dissolved in toluene (50 mL). To this solution was added 4-fluorophenyl boronic acid (2.52 g, 18.0 mmol), tetrakis (triphenylphosphine)palladium (0) (0.58 g, 3 mole%), potassium carbonate (4.56 g, 33.0 mmol) and water (25 mL) and the resulting mixture refluxed for 18 hours after which time the layers were separated. The organic layer was evaporated to a crude solid which was recrystallized from ethanol-water to give 2-nitro-5-(4-fluoro)phenylthiophene (2.99 grams (80%)]. Mp 129°–130° C.

The above biaryl compound (2.89 g, 12.9 mmol) was dissolved in a 1:1 mixture of acetic acid-acetic anhydride (50 mL). To this was added iron powder (2.89 g, 51.7 mmol) and the resulting mixture stirred at 80° C. for 5 hours after which time the mix was poured into ice-water and the crude solid filtered and washed with water. Recrystallization from ethanol-water yields N-5-[(4-fluoro)phenyl-thien-2-yl] acetamide [2.60 grams (86%)]. Mp 141°–142° C.

The above acetamide (2.52 g, 11.0 mmol) was dissolved in anhydrous tetrahydrofuran (50 mL) and cooled to –78° C. To this was added lithium diisopropylamide (7.33 mL of 1.5M sol'n) and methanesulfonyl chloride (0.85 mL, 11.0 mmol). The mix was stirred for 30 minutes before it was evaporated in vacuo and redissolved in methanol (50 mL). Concentrated ammonium hydroxide (5 mL) was added and this was stirred for 30 minutes after which time the mix was again evaporated in vacuo and the product extracted with ethyl acetate. The organic layer was washed with 1N HCl then water and concentrated in vacuo. Purification on a silica gel column eluted with hexane-ethyl acetate 3:1 gave the title compound [0.69 g (23%)]. Mp 185.5°–187° C., CIMS (m/e) 272 (MH⁺).

Substitution of phenyl boronic acid for 4-fluorophenyl boronic acid in the above procedure yields N-5-[phenyl-thien-2-yl]methanesulfonamide (33) as a white solid, Mp 180°–181° C., CIMS (m/e) 254 (MH⁺).

Method 5: General Procedure for the Synthesis of Compounds V

2-Nitro-3-bromothiophene [Ann. Chem., 512,136 (1934)] (1 equivalent) is dissolved in dimethylformamide (5 mL per mmol) and to the resulting solution is added the appropriately substituted phenol (1 equivalent) and potassium carbonate (2 equivalents). This mixture is stirred for 4–8 hours at 80° C. and then poured into water and the solid filtered, washed with water and dried in vacuao to give the intermediate 2-nitro-3-phenoxythiophene.

The above substituted 2-nitro-3-phenoxythiophene (1 equivalent) is suspended in concentrated HCI (4 mL per mmol). Tin powder (3 equivalents) is added and the mixture stirred at 50°–70° C. for 4–6 hours after which time the resulting solid is filtered, washed with ether and dried in vacuo to give the tin double salt. The tin salt is dissolved in pyridine (10 mL per mmol) and cooled to 0° C. Methanesulfonyl chloride (1 equivalent) is added, stirred for 16–20 hours and poured into water. The product is extracted with ethyl acetate, the organic layer washed with 1N HCI, then water and dried over magnesium sulfate. The resulting 2-methanesulfonamido-3-phenoxy thiophene is purified via silica gel column chromatography eluted with hexane-ethyl acetate.

The compounds of Table 4 were prepared according to the general cedure described above in Method 5.

TABLE 4

| Example Number | R | Melting Point °C. | Analysis+ C,H,N | Mass Spectrum m/e (M+) |
|---|---|---|---|---|
| 34 | 4-F | gum | x,x,x | 288 |
| 35 | H | 98–101.5 | x,x,x | 270 |
| 36 | 2,4-diF | gum | x,x,x | 306 |
| 37 | 3-Ph | gum | x,x,x | 346 |
| 38 | 2,4-diCH$_3$ | 82–89 | x,x,x | 298 |
| 39 | 4-CF$_3$ | 100–104 | x,x,x | 338 |
| 40 | 3-F | gum | x,x,x | 288 |
| 41 | 2-Ph | 107–111 | x,x,x | 346 |
| 42 | 4-F,2-CH$_3$ | gum | x,x,x | 302 |
| 43 | 3,4-diOCH$_3$ | 135–137 | x,x,x | 330 |
| 44 | 1-Naphthyl | 37–45 | x,x,x | 320 |
| 45 | 2-Naphthyl | gum | x,x,x | 320 |

Biological Results

Procedure I

RBL-1 cell 5-lipoxygenase and cyclooxugenase - Homogenate

Rat basophilic leukemia cells (RBL-1; $5 \times 10^7$ viable cells/mL) were disrupted by homogenization on ice (four 20 sec bursts) with a Brinkman polytron. Complete cell breakage was verified microscopically. The homogenate was then centrifuged at 9,220×g for 48 minutes at 4° C. The pellet was discarded and the supernatant was saved as the source of enzymes. The supernatant was pre-incubated for five minutes at 37° C. in the presence of 2 mM of CaCl2 and compound or vehicle (1% DMSO). The conversion of AA into products by CO and LO was initiated by adding 10 µL (50 µCi) of 1-$^{14}$C-AA to each tube and incubated at 37° C. for 20 minutes. The reaction was stopped by adjusting the pH of each sample to 3 to 3.5 with 2M formic acid. Samples were extracted with three volumes of chloroform to isolate the products of 5-LO formed during the reaction. Fractions were dried under nitrogen, then resuspended in 40 µL of chloroform and spotted onto silica gel HL plates. The plates were developed in A-9 solvent. The dried plates were analyzed using a Bioscan Imaging TLC scanner to determine the percentage of radiolabelled M converted to 5-HETE (LO product) and PGD$_2$ (CO product) in each sample.

Procedure II

RBL-1 Cell 5-Lipoxygenase and cyclooxygenase - Whole cells

The ability to inhibit 5-LO and CO in intact RBL-1 cells was also evaluated. RBL-1 cells were maintained in culture in minimal essential medium (Bio*Whittaker, Walkersville, Md.), containing 12.5% fetal calf serum, 10 mg/mL streptomycin, 10 I.U./mL penicillin G, 50 mg/mL gentamycin and 2 mM L-glutamine (Bio*Whittaker, Walkersville, Md.). Cells were collected by centrifugation, washed once in HBSS, and resuspended at a concentration of $1 \times 10^5$ cells/mL. Cells were incubated in the presence of vehicle or drug then centrifuged at 800×g for 10 minutes at 4° C. The supernatant was removed by aspiration and the cells were resuspended in 0.5 mL of HBSS. The reaction was started by the addition of 20 µg/mL of calcium ionophore A 23187 (mixed calcium and magnesium salts, Calbiochem, La Jolla Calif.) and allowed to proceed for 15 minutes, then stopped by plunging the tubes into a slush ice bath. The conversion of M to 5-LO products was initiated by the addition of 10 µL (50 uCi) of 1-$^{14}$C-AA. Products were isolated by acidification and extraction, followed by thin layer chromatography analysis as described above. Radioactive areas corresponding to authentic 5-LO (5-HETE) and CO (PGD2) products were quantitated by the Bioscan 2000 Imaging System.

Procedure III

Human Prostaglandin H$_2$ Synthase Typ II (Cox-2) Whole Cell Assay (Multiple Concentrations)

ECV-304 (human, endothelial, umbilical cord) cells are maintained in culture in a suitable medium, and are trypsinized and plated at a density of 1×106 cells per well of a 6 well plate prior to assay. Approximately 28 hours later, 50 µg/ml PMA and 1 mM ionomycin (both final concentrations) are added to each well and incubated for an additional 16 hours. Vehicle or test compounds are incubated with the cells for five minutes prior to initiation of Cox-2 enzyme activity by the addition of 30 µM arachidonic acid. Ten minutes later, an aliquot of the supernatant is withdrawn and the amount of PGE$_2$ present quantitated by radioimmunoassay. Activity, reported as percent inhibition of PGE$_2$ produced, is calculated as follows:

| Example # | Procedure III (COX-2) Wh Cell 1% @ 10 µM IC$_{50}$ (µM) | Procedure II (5-LO) Wh Cell IC$_{50}$ (µM) | Procedure I (5-LO) Homog. IC$_{50}$ (µM) |
|---|---|---|---|
| 2 | 4.22 | 0.47 | 0.07 |
| 12 | 18 | 0.66 | 0.075 |
| 13 | 5.8 | 0.65 | 0.09 |
| 15 | 1.69 | 0.31 | 0.12 |
| 3 | 13% | 0.49 | 0.16 |
| 14 | 1.97 | 0.73 | 0.15 |
| 4 | 39% | 0.66 | 0.10 |
| 1 | 1.81 | 0.46 | 0.13 |
| 11 | 1.18 | 0.31 | 0.02 |
| 21 | 3.0 | 0.80 | 0.07 |
| 6 | 5.3 | 0.89 | 0.03 |
| 7 | 0% | 1.45 | 0.02 |
| 28 | 33% | 0.7 | 0.19 |
| 8 | 10.3 | 0.5 | 0.06 |
| 9 | 54% | 0.66 | 0.06 |
| 33 | 31% | 0.79 | 0.11 |
| 22 | 10 | 0.77 | 0.06 |

-continued

| Example # | Procedure III (COX-2) Wh Cell 1% @ 10 μM IC$_{50}$ (μM) | Procedure II (5-LO) Wh Cell IC$_{50}$ (μM) | Procedure I (5-LO) Homog. IC$_{50}$ (μM) |
|---|---|---|---|
| 24 | 10 | 1.12 | 0.36 |
| 25 | 16% | 1.04 | 0.05 |
| 27 | 44% | 0.9 | 0.10 |
| 26 | 8% | 2.9 | 0.30 |
| 5 | 0% | 38.5 | 1.8 |
| 10 | 1.02 | 0.78 | 0.06 |
| 16 | 1.90 | 1.09 | 0.09 |
| 23 | 10 | 0.5 | 0.05 |
| 20 | 36% | 4.7 | 0.61 |
| 31 | 45% | 0.38 | 0.11 |
| 29 | 9.10 | 2.39 | 0.07 |
| 17 | 5.29 | 1.4 | 0.06 |
| 30 | 2.76 | 0.63 | 0.04 |
| 18 | 8% | 6.5 | 0.31 |
| 19 | 29% | 1.8 | 0.14 |
| 32 | 3% | 2.1 | 0.15 |

$$\% \text{ Inhibition} = \left(1 - \frac{\text{PGE2 produced in treated sample}}{\text{PGE2 produced in vehicle sample}}\right) \times 100$$

The compounds of Table 4 (34–45) were evaluated in Procedures I-III. The compounds were found to be inhibitors of Cox-2 activity (Procedure I) but were ineffective as inhibitors of 5-LO (Procedures II and III) in either cell free or whole cell assays.

Procedure IV
Carrageenan-Induced Localized Inflammation In Subcutaneous Chambers Implanted In Beagle Dogs Sterile perforated teflon chambers (wiffle golf balls) were surgically implanted subcutaneously in the dorsal neck fold of beagle dogs (8–13 kg, mixed sex). After a recovery period of 1 month, a 1 ml sample of fluid exudate from each dog was aspirated from within the chamber using a 1 ml syringe and 20 gauge 1 inch needle inserted through one of the perforations in the ball. Immediately after obtaining the sample, 1.5 ml of 0.33% sterile carrageenan lambda (Sigma Chemical Co., St. Louis, Mo.) was injected into the chamber. Dilutions of the baseline samples were made in saline and analyzed for leukocyte count using a Coulter Counter (6.08–50 μm range). The sample was also analyzed for concentrations of PGE2 and LTB4 by adding 200 μl of sample to 1 ml ethanol and centrifuging the precipitate (1,500 X g, 7 min). The supernatant was aspirated and stored at 0° C. until enzyme linked immunosorbant assays (ELISAs) were performed (ELISA Technologies, Lexington, Ky.). Samples were also drawn at 5 and 24 hours post carrageenan challenge and treated in a similar manner. Local inflammation is characterized by elevated levels of eicosanoids (PGE$_2$ and LTB$_4$) and by an influx of leukocytes into the chamber. Elevated levels of PGE$_2$ in the fluid exudate is indicative of an inducable cyclooxygenase-2 (COX-2) mediated response.

Blood samples were drawn simultaneously with the fluid exudates for evaluation of non-inflammatory production of eicosanoids. Samples were collected with 4.5 ml lithium-heparin monovettes (Sarstedt) and Vacutainer blood collection sets (21 G ¾inch). One ml of each blood sample was treated with 50 μl calcium ionophore A23187 (0.28 mg/ml suspended in 4% DMSO/HBSS), followed by a 15 minute incubation at 37° C. The reaction was stopped by placing the samples in an ice slush bath for 5 minutes. The samples were then centrifuged (1,500 X g, 7 minutes), and 100 μl plasma were added to 1 ml cold methanol to extract the eicosanoids. The extracted samples were centrifuged (1,500 X g, 7 minutes) and the supernatant stored at 0° C. until ELISAs were performed to evaluate eicosanoid (PGE$_2$ and LTB$_4$) production. Since the PGE$_2$ produced in peripheral blood is derived mainly from the platelets, it is indicative of the constitutive COX-1 response.

Drug effects can be evaluated on several important aspects of inflammation using this in-vivo assay. Inhibition of leukocyte influx by administration of a therapeutic agent at the time of carrageenan challenge represents anti-inflammatory activity. PGE$_2$ and/or LTB$_4$ inhibition may give some insight into the mechanism of action of the agent. Selectivity of a COX inhibitor can be determined by comparing PGE$_2$ inhibition in peripheral blood (COX-1) to that of the inflammatory fluid exudate in the chamber (COX-2).

Figure 1:
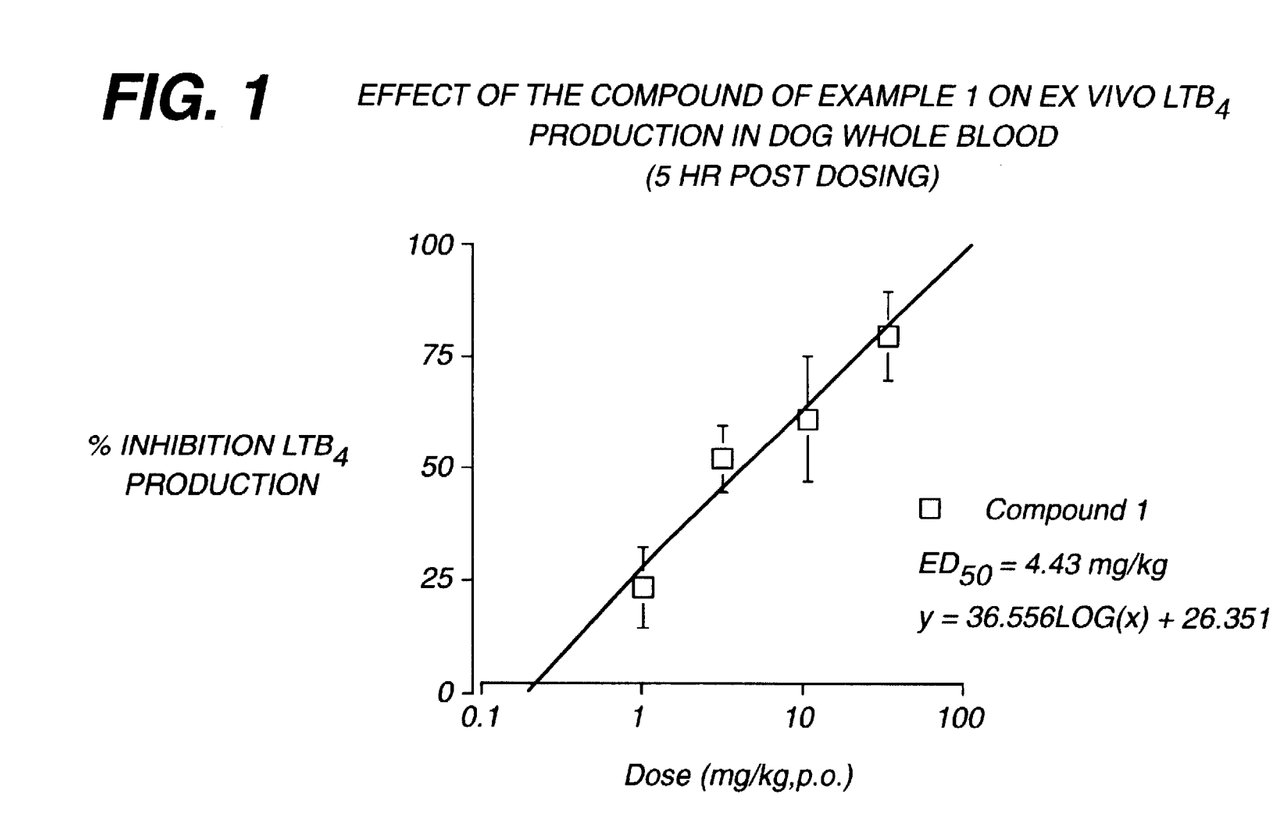
FIG. 1 graphically depicts the effects of the compound of Example 1 on ex vivo $LTB_4$ production in dogs five hours following oral administration of compound.

The dog inflammation model described in Procedure IV allows for the simultaneous evaluation of eicosanoid production in the periphery and at a site of inflammation. FIG. 1 graphically depicts the effects of compound 1 on ex vivo LTB$_4$ production in dogs five hours following oral administration of compound. The results indicate that compound 1 inhibited peripheral LTB4 production (IC$_{50}$ =4.4 mg/kg) five hours after oral administration of compound. No inhibition of LTB$_4$ production in whole blood was detected at 24 hours following dosing. When the exudate in the inflammatory chambers was examined, compound 1 caused a dose related inhibition of both the accumulation of inflammatory cells in the exudate and LTB$_4$ levels measured in the fluid. The ED$_{50}$ for inhibition of both cellular influx and fluid LTB$_4$ levels was <0.01 mg/kg. These data indicate that compound 1 is an orally active and potent inhibitor of an inflammatory event (cell infiltration) which is thought to be mediated by products (LTB$_4$) of 5-LO.

What is claimed is:

1. A compound having a structure that corresponds to the formula I:

wherein,

R$_2$ is CF$_3$, C$_1$–C$_{10}$ alkyl, or phenyl;

X is O, S, or CH$_2$; and

R is aryl, C$_1$–C$_{10}$ alkyl, or C$_3$–C$_8$ cycloalkyl, wherein aryl is a phenyl or naphthyl moiety which may be substituted by one or more of the following: halogen, CF$_3$, C$_1$–C$_4$ alkyl, alkoxy, alkylthio, or alkylsulfonyl; and the pharmaceutically acceptable salts, esters and pro-drug forms thereof.

2. A compound according to claim 1 having a structure corresponding to the Formula II:

wherein,

R$_1$ is halogen, CF$_3$, C$_1$–C$_4$ alkyl, alkoxy, alkylthio, or alkylsulfonyl.

3. The compound according to claim 1, N-[5-Phenoxythien-2-yl]methanesulfonamide.

4. The compound according to claim 1, N-[(3-Methyl)-5-phenoxythien-2-yl]methanesulfonamide.

5. The compound according to claim 1, N-[(4-Fluoro-3-methyl)-5-phenoxythien-2-yl]methanesulfonamide.

6. The compound according to claim 1, N-[(3-Trifluoromethyl)-5-phenoxythien-2-yl]methanesulfonamide.

7. The compound according to claim 1, N-[(2,4-Dichloro)-5-phenoxythien-2-yl]methanesulfonamide.

8. The compound according to claim 1, N-[5-Phenoxythien-2-yl]benzenesulfonamide.

9. The compound according to claim 1, N-[(4-Fluoro-2-methyl)-5-phenoxythien-2-yl]methanesulfonamide.

10. The compound according to claim 1, N-[(2,4-Difluoro)-5-phenoxythien-2-yl]methanesulfonamide.

11. The compound according to claim 1, N-[5-(1-Naphthoxy)thien-2-yl]methanesulfonamide.

12. The compound according to claim 1, N-[5-Thiopentyl-thien-2-yl]methanesulfonamide.

13. The compound according to claim 1, N-[5Phenoxythien-2-yl]isopropylsulfonamide.

14. The compound according to claim 1, N-[(4-fluoro)-5phenoxythien-2-yl]methanesulfonamide.

15. A pharmaceutical composition for the alleviation of inflammatory disorders in mammals comprising a therapeutically effective amount of a compound in accordance with claim 1 in association with a pharmaceutically acceptable carrier.

16. A method of alleviating inflammation in a mammal exhibiting an inflammatory condition comprising administering to said mammal a pharmaceutical composition according to claim 15.

* * * * *